United States Patent [19]

D'Amelio

[11] Patent Number: 4,721,097
[45] Date of Patent: Jan. 26, 1988

[54] ENDOSCOPE SHEATHS AND METHOD AND APPARATUS FOR INSTALLATION AND REMOVAL

[75] Inventor: Frank D. D'Amelio, Naugatuck, Conn.

[73] Assignee: Circon Corporation, Santa Barbara, Calif.

[21] Appl. No.: 925,603

[22] Filed: Oct. 31, 1986

[51] Int. Cl.$^4$ .............................................. A61B 1/00
[52] U.S. Cl. ........................................... 128/4; 53/585
[58] Field of Search ................. 128/4, 6; 53/585, 292

[56] References Cited

U.S. PATENT DOCUMENTS

| | | | |
|---|---|---|---|
| 2,976,661 | 3/1961 | Bagnelle | 53/585 X |
| 3,144,020 | 8/1964 | Zingale | 128/4 |
| 3,162,190 | 12/1964 | Del Gizzo | 128/6 |
| 3,794,091 | 2/1974 | Ersek et al. | 128/23 X |
| 3,809,072 | 5/1974 | Ersek et al. | 128/23 |
| 3,841,940 | 10/1974 | Rubinich | 53/585 X |
| 4,286,421 | 9/1981 | Fujio | 53/292 X |
| 4,646,722 | 3/1987 | Silverstein et al. | 128/4 |

Primary Examiner—William H. Grieb
Attorney, Agent, or Firm—Perman & Green

[57] ABSTRACT

An endoscope and a disposable sanitary sheath are disclosed. In the preferred embodiment the core of the endoscope has indentations longitudinally extending along its exterior surface in a peanut-like cross-sectional configuration while the sheath has channels within longitudinally extending thicker portions. The sheath is positionable on the endoscope core with its thickened portions located within the indentations. Alternate embodiments are disclosed as are the method and apparatus for placing sheaths on endoscope cores and their removal.

17 Claims, 16 Drawing Figures

ENDOSCOPE SHEATHS AND METHOD AND APPARATUS FOR INSTALLATION AND REMOVAL

BACKGROUND OF THE INVENTION

1. Field of the Invention

This invention relates to endoscopy and more particularly, to endoscopes and sanitary disposable sheaths usable together for physical examinations as well as to a method and apparatus for installing and removing sheaths from endoscopes.

2. Description of the Prior Art

To insure quality health care for the general public, there is an ever increasing need for cost efficient procedures as well as for effective, convenient, reliable, sterile instruments. These needs principally arise from the uncompromisable requirement for patient safety. Such safety is becoming more difficult to achieve due to increasing problems with new contagious viruses. Consider, for example the spread of acquired immune difficiency syndrome, AIDS. Unsanitized instruments have been clearly demonstrated to be one of the causes for this particular risk to patient health.

To a certain extent, cost effectiveness is as important to the health care of a population as is the quality of the care itself. If costs become prohibitive, health care will not be sought. The skyrocketing of insurance premiums compounds this cost burden for both physicians and patients alike. Effective, convenient, reliable, sterile, cost efficient instruments and procedures are thus important factors in insuring quality health care for a population generally.

Endoscopic examinations constitute a medical procedure for viewing and treating internal organs and passages of a patient. Endoscopes, the instruments employed in endoscopic examinations have long been used for a wide variety of diagnostic and therapeutic purposes. Through time, their designs have been tailored to best achieve their particular purposes. The apparatus and methods which pertain to one type of endoscope are generally applicable to all types of endoscopes. For the sake of simplicity, therefore the endoscopes described and discussed herein will be limited to those designed for examining and treating the rectum and sigmoid colon of a patient. Such instruments are known as sigmoidoscopes, preferably flexible sigmoidoscopes.

Sigmoidoscopes are utilized in environments which necessitate their sterilization or sanitization between patients. Although a sterilized sigmoidoscope or other endoscope is normally utilized by the physician on a patient for only a short period of time, as for example a typical time period of about ten to forty minutes the sterilization thereafter in preparation for the next subsequent patient examination requires a long period of time, as for example many hours. The cost for an examination is therefore artificially increased due to the time and cost of sterilizing the instrument. This tends to drive up the cost of medical treatment when an endoscope is used. One solution would be to maintain a large supply of endoscopes for simultaneously sterilizing a large quantity at one time and thereby drive down the unit time and cost for the sterilization of each instrument. Endoscopes, however, are precision instruments and quite costly. Maintaining a full day's supply of such instruments for batch sterilization over night is an expense which need not be incurred if a thorough and rapid sanitization procedure were available.

The complexity of endoscope construction contributes to the complexity and cost of their sterilization. Their external surfaces may be adequately sterilized in a relatively short time. However, endoscopes normally include channels for the purpose of remotely guiding water, air, suction, biopsies and the like. Such channels are of small diameters and extend the entire length of the endoscope core. These channels may be contacted by bodily fluids and tissues during an examination. Therefore, in addition to the external surfaces, these channels require sterilization between usages, and it is these channels which present the complexitites, difficulties and time problems in sterilization. Among the more effective methods for sterilizing endoscopes is chemical vapor treatment. Such vapors, however, are toxic and potentially injurious to the person conducting the sterilization. Although effective, such method still retains the time and cost problems while creating the additional problem of safety to the employees and the environment.

In many segments of the health care field, problems of disease transmission from one patient to the next have been solved through the ever increasing utilization of disposable instruments or shields. These types of solutions have not found wide acceptance in the field of endoscopy despite the recognized benefits which would be realized. This is due in large part to the complexity of endoscopes as discussed above, particularly since their internal channels are hard to clean and are used as conduits for bodily fluids and tissues as may be needed for taking biopsies.

One approach to the disposable, sanitary shielding of endoscopes is a shield that is rolled onto the endoscope from the front or distal end toward the back or proximal end. An aperture or apertures in the distal end of the shield must be aligned with the channel or channels of the endoscope prior to the initiation of the rolling so as to permit the endoscope channels to function in their intended manners. Even if the shield is installed properly, bodily fluid and tissue may still contact non-disposable portions of the endoscope such as in its internal tubing and channels and thus may require sanitization of the entire endoscope between usages from one patient ot the next.

As illustrated by a large number of prior approaches, continuing efforts are being made in an attempt to solve the problem of efficiently, conveniently reliably and economically shielding medical instruments for sanitary purposes. None of the known approaches however, teaches or suggests the present inventive combination of component elements as disclosed herein. The present invention achieves its purposes, objectives, and advantages over the prior approaches, conveniently and reliably through a new, useful, and unobvious combination of component elements and method steps, at a great reduction in time and cost, and through the utilization of only readily available materials and conventional components.

These purposes, objectives and advantages should be construed as merely illustrative of some of the more prominent features and applications of the present invention. Many other beneficial results can be attained by applying the disclosed invention in a different manner or by modifying the invention within the scope of the disclosure. Accordingly, other purposes, objects, and advantages as well as a fuller understanding of the invention may be had by referring to the summary of the invention and detailed description describing the preferred embodiments in addition to the scope of the invention as defined by the claims taken in conjunction with the accompanying drawings.

SUMMARY OF THE INVENTION

The present invention is defined by the appended claims with the specific preferred embodiments shown in the attached Figures. For the purposes of summarizing the invention, the invention may be incorporated into an improved combination of an endoscope and a sheath for use in physical examinations. The combination comprises an endoscope having a cylindrically shaped core with a first distal end which terminates and with a headpiece at the other end. The combination also comprises a disposable sheath removably positionable over the core. The sheath has a tubular portion with a first or distal end which is basically closed and a second or proximal end which is open. The sheath also has at least one enlarged longitudinal portion extending along the length thereof with the possibility of one or more tubular channels extending the length of the enlarged longitudinal portion. The tubular channels would be within the enlarged or thicker longitudinal portion of the sheath while the remainder of the sheath would be relatively thinner than the enlarged longitudinal portion. The cross-section of the core includes at least one longitudinal recess or concave portion on its surface with the enlarged longitudinal portion of the sheath positionable in the recess. The core may have two recessed portions to form a peanut-shaped, cross-sectional configuration and the sheath may have two enlarged longitudinal portions positionable in the recesses. The core may have a circular cross-sectional configuration, the sheath having at least one enlarged longitudinal portion and the combination also including an intermediate cylindrical sleeve positionable between the core and the sheath with at least one longitudinal recess in its exterior surface for receiving the enlarged longitudinal portion. The endoscope may have a circular cross-sectional configuration while the sheath may have radially inwardly directed supports receivable on the external surface of the core. The core may have a circular cross-sectional configuration and the remainder of the sheath being thinner than the enlarged longitudinal portion of the sheath to render the combination of a non-circular, cross-sectional configuration. The core may have a circular, cross-sectional configuration and the sheath may have two or more enlarged longitudinal portions to render the combination of a non-circular, cross-sectional configuration. The enlarged longitudinal portions may be located 90 degrees, 180 degrees, or any other angular placement from each other.

The invention may also be incorporated into an improved combination for use in physical examinations. The combination comprises an endoscope having a distal end and a headpiece with a cylindrical core therebetween. At least one cylindrical optical means extends axially along the length of the endoscope for the remote viewing of a patient. The core has no channel means extending along its length except for that containing the optical means. The cross-sectional configuration of the core includes at least one indented portion extending along its length. The combination also includes a sheath having a closed, transparent distal end and an open proximal end with a tubular portion therebetween. The sheath has at least one longitudinal thick portion along the length thereof with a tubular channel extending the length of the thick portion. The sheath is removably positionable on the endoscope with the channel located in operative association with the indented portion. The core may be constructed of a plurality of connectable segments, each having two or more indentations which may be disposed at 180 degrees from each other in a peanut-like or watch-glass, cross-sectional configuration, or the indentations may be disposed at a 90 degree or any other angular placement from each other, the indentations extending the length of the core for the receipt of two thick portions of the sheath. The combination further includes a cylindrical sleeve positioned over the segments. The segments may be couplable one to another in pairs, each pair being located at an angle from the next adjacent pair for allowing the full flexibility of the core in two meridians. The segments may be couplable one to another in pairs, each pair being axially aligned with the next adjacent pair for allowing the flexability of the core in one or two mreidians. The segments may also be coupled one to another in a spiral for allowing the full flexability of the core in two meridians. The core may be constructed of a cylindrical extrusion having a plurality of indentations positioned with respect to each other in a non-circular, cross-sectional configuration extending the length of the core for the receipt of a plurality of thick portions of the sheath.

The invention may further be incorporated into an improved combination for use in physical examinations. The combination comprises an endoscope having a distal end and a headpiece with a core therebetween. The combination also includes a sheath having a closed distal end and an open proximal end with a tubular portion therebetween. The sheath has at least one longitudinally extending portion thicker than the remainder of the sheath extending along the length of the sheath from adjacent the proximal end of the sheath to adjacent the distal end of the sheath with a tubular channel extending the full length of the thicker portion. The sheath is removably positionable on the core. The sheath may include one thicker portion with a plurality of channels therein with the axes of the channels located radially exteriorly of the external surface of the core. The sheath may include two thicker portions with a channel in each thicker portion and with the axes of the channels located radially exeriorly of the external surface of the core. The sheath may include two thicker portions with a channel in each thicker portion and with the axes of the channels located radially interiorly of the radially outermost surface of the core.

In addition, the invention may be incorporated into an improved combination for use in physical examinations. The combination comprises an endoscope having a core with a distal end and with a headpiece at the other end. At least one cylindrical optical means extends axially along the length of the core for the remote viewing a patient, the core being devoid of channel means extending along its length except for the optical means. The cross-sectional configuration of the core includes at least one longitudinal recess extending along the exterior surface of the core. The combination also includes a sheath having a tubular section with a closed, transparent distal end and with an open proximal end. The sheath has having at least one longitudinally extending enlarged portion, the remainder of the sheath being thinner than the enlarged portion. The enlarged portion extends along the length of the sheath from adjacent the proximal end of the sheath to adjacent the distal end of the sheath with a tubular channel within the length of the enlarged portion. The sheath is removably positionable on the core with the channel located within the recess.

The invention may further be incorporated into an improved disposable, sanitary sheath for use with an endoscope and formed of an elastomeric, fluid impervious material and configured to have a closed first end and an open second end with a tubular portion therebetween. The sheath has at least one longitudinal thick portion along the length thereof from the first end to the second end and with a tubular channel extending the length of the longitudinal portion. Channel openings are provided adjacent the first end and adjacent the second end for the transmission of fluids through the channel coupling the channel openings. The sheath may include one thick portion, thicker than the remainder of the sheath, with a plurality of channels therein and with the axes of the channels located radially exeriorly of the external surface of the core. The sheath may include two thick portions, thicker than the remainder of the sheath, with a channel in each thick portion and with the axes of the channels located radially exeriorly of the external surface of the core. The sheath may include two thick portions, thicker than the remainder of the sheath, with a channel in each thick portion and with the axes of the channels located radially interiorly of the radially outermost surface of the core. The front face or basically closed end of the sheath is transparent.

Additionally, the invention may be incorporated into an improved endoscope for use with a disposable sheath and having a first end and a second end and a core therebetween. At least one cylindrical optical means is provided within of the core and extends axially along the length of the core for the remote viewing of a patient when using the endoscope for examination purposes. The core has no channel means extending along its length except for that containing the optical means. The cross-sectional configuration of the core has at least one indented portion along its length from adjacent the first end to adjacent the second end. The core may be constructed of a plurality of connectable segments, each may have two indentations disposed at 180 degrees from each other in a peanut-like, cross-sectional configuration, or the indentations may be disposed at a 90 degree or any other angular placement from each other, the indentations extending the length of the core for the receipt of two thick portions of the sheath, and further including a cylindrical sleeve positioned over the segments. The segments may be couplable one to another in pairs, each pair being 90 degrees from the next adjacent pair for allowing the full flexability of the core in two meridians. In the alternative, the segments may be couplable one to another in pairs, each pair being axially aligned with the next adjacent pair for allowing the flexability of the core in one meridian. The segments may be coupled one to another in a spiral for allowing the full flexability of the core in all meridians. The core may be constructed of a cylindrical extrusion having two indentations disposed at 180 degrees from each other in a peanut-like, cross-sectional configuration, or the indentations may be disposed at a 90 degree or any other angular placement from each other, the indentations extending the length of the core for the receipt of two thick portions of the sheath.

The invention may yet further be incorporated into apparatus to facilitate the placement of a sheath upon the core of an endoscope and to facilitate its removal therefrom. The apparatus comprises a tube of relatively rigid, air-impervious material having an internal configuration similar to that of the core upon which the sheath is to be placed but of a slightly larger cross-sectional configuration. The tube has a closed distal end and an open proximal end for receiving the endoscope, the proximal end being provided with a removable first cap axially located with respect to the tube and the tube being provided with a second removable cap at an intermediate portion of the tube and radially located with respect to the tube. There may also be more than one intermediate removable cap in the event that the port at the first intermediate cap becomes clogged with foreign material. The sheath may be inserted into the tube with the first cap removed and the second cap unremoved to maintain the air pressure within the tube greater interior of the sheath than exterior of the sheath for holding the sheath in position against the interior surface of the tube for thereby allowing the positioning of the endoscope within the sheath and tube. The radial cap is removable for the relief of the lower pressure exterior of the sheath for the release of the sheath from the tube and onto the core. A coupling lip is provided on the tube for supporting the radial cap and, in the absence of the cap, for coupling with a source of negative pressure whereby when a core with a sheath thereon is positioned within the tube. A vacuum may be drawn through the lip in the tube external of the sheath to pneumatically separate and remove the sheath from the endoscope after the completion of an endoscopic procedure. The entire pack can now be conviently and neatly disposed of.

Moreover, the invention may be incorporated into apparatus to facilitate the placement of a sheath upon the core of an endoscope. The apparatus comprises a tube of relatively rigid, air-impervious material having an internal configuration similar to that of the core upon which the sheath is to be placed but of a slightly larger cross-sectional configuration. The tube has a closed distal end and an open proximal end for receiving the endoscope. The proximal end is provided with a removable first cap axially located with respect to the tube. The tube is provided with a second removable cap at an intermediate portion of the tube and radially located with respect to the tube whereby a sheath may be inserted into the tube with the first cap removed and the second cap unremoved to maintain the air pressure within the tube greater interior of the sheath than exterior of the sheath for holding the sheath in position against the interior surface of the tube for thereby allowing the positioning of the core within the sheath and tube. The radial cap is removable for the relief of the lower pressure exterior of the sheath for the release of the sheath from the tube and onto the core.

The invention may yet further be incorporated into apparatus to facilitate the removal of a sheath from the core of an endoscope. The apparatus comprises a tube of relatively rigid, air-impervious material having an internal configuration similar to that of the core with the sheath thereon but of a slightly larger cross-sectional configuration. The tube has a closed distal end and an open proximal end for receiving the core with the sheath thereon. The proximal end is provided with a removable first cap axially located with respect to the tube. The tube is provided with a second removable cap at an intermediate portion of the tube and radially located with respect to the tube whereby an endoscope with a sheath thereon may be inserted into the tube with the first and second caps removed. A coupling lip on the tube supports the second or radial cap and, in the absence of the radial cap, couples with a source of negative pressure whereby when a core with a sheath thereon is positioned within the tube, a vacuum may be drawn through the lip in the tube external of the sheath to pneumatically separate and remove the sheath from the endoscope. The apparatus further includes suction means to create the vacuum for removing the sheath from the endoscope.

The invention may yet further be incorporated into a method to place a sheath upon the core of an endoscope and to remove it therefrom. The method includes the steps of providing a tube of relatively rigid, air-impervious material having an internal configuration similar to that of the core to be provided with the sheath but with a cross-sectional configuration slightly larger than that of the core. The tube has a distal end which is closed and a proximal end which is open for the receipt of the core. A sheath is positioned within the tube and is supported against the interior surface of the tube by a pressure differential between the interior and exterior of the sheath. A core is then inserted into the tube and the pressure differential equalized between the interior and exterior surfaces of the sheath for the release of the elastomeric sheath from the tube and its placement onto the core. The core with the sheath is then removed from the tube. A core with a sheath is then inserted into the tube. A vacuum is then drawn in the tube between the tube and the sheath to pneumatically remove the sheath from the core.

Additionally, the invention may further be incorporated into method to facilitate the placement of a sheath upon the core of an endoscope and its removal therefrom. The method includes the steps of providing a tubular member of relatively rigid, air-impervious material having an internal configuration similar to that of the core to be provided with the sheath but with a cross-sectional configuration slightly larger than that of the core. The tubular member has a distal end which is closed and a proximal end which is open for the receipt of the core and a second opening intermediate the ends. A sheath is positioned within the tubular member and supported against the interior surface of the tubular member by a pressure between the interior and exterior of the sheath. A cap is removed from the open end of the tubular member and a core inserted into the tubular member. A cap is then removed from the second opening to equalize the pressure differential between the interior and exterior surfaces of the sheath for the release of the sheath from the tube and its placement onto the core. The core with the sheath is then removed from the tube. After an endoscopic procedure, the core with a sheath is then inserted into the tubular member and a vacuum drawn in the tube between the tube and the sheath through the second opening to pneumatically remove the sheath from the core.

Yet further, the invention may be incorporated into a method of placing a sheath upon the core of an endoscope. The method includes the steps of providing a tube of relatively rigid, air-impervious material having an internal configuration similar to that of the core to be provided with the sheath but with a cross-sectional configuration slightly larger than that of the core. The tube has a distal end which is closed and a proximal end which is open for the receipt of the core. A sheath is then positioned within the tube and supported against the interior surface of the tube by a pressure differential between the interior and exterior of the sheath. An endoscope is inserted into the tube and the pressure differential between the interior and exterior surfaces of the sheath is equalized for the release of the sheath from the tube and its deposition onto the endoscope.

Lastly, the invention may be incorporated into a method of removing a sheath from an endoscope. The method includes the steps of providing a tube of relatively rigid, air-impervious material having an internal configuration similar to that of the core to be provided with the sheath but with a cross-sectional configuration slightly larger than that of the endoscope with the sheath. The tube has a distal end which is closed and a proximal end which is open for the receipt of the endoscope. An endoscope shielded by a sheath is inserted into the tube and a vacuum drawn in the tube between the tube and the sheath to pneumatically remove the sheath from the endoscope.

The foregoing has outlined rather broadly the more pertinent and important features of the present invention in order that the detailed description of the invention that follows may be better understood and whereby the present contribution to the art can be more fully appreciated. Additional features of the invention will be described hereinafter which form the subject of the claims of the present invention. It should be appreciated by those skilled in the art that the conception and the specific embodiments disclosed herein may be readily utilized as a basis for modifying or designing other apparatus and methods for carrying out the same purposes of the present invention. It should also be realized by those skilled in the art that such equivalent constructions and methods do not depart from the spirit and scope of the invention as set forth in the appended claims.

BRIEF DESCRIPTION OF THE DRAWINGS

For a more complete understanding of the nature, objects, and advantages of the present invention, reference should be had to the following detailed description taken in conjunction with the accompanying drawings wherein.

Similar numerals refer to similar parts throughout the various Figures.

DETAILED DESCRIPTION OF THE INVENTION

Figure 1:
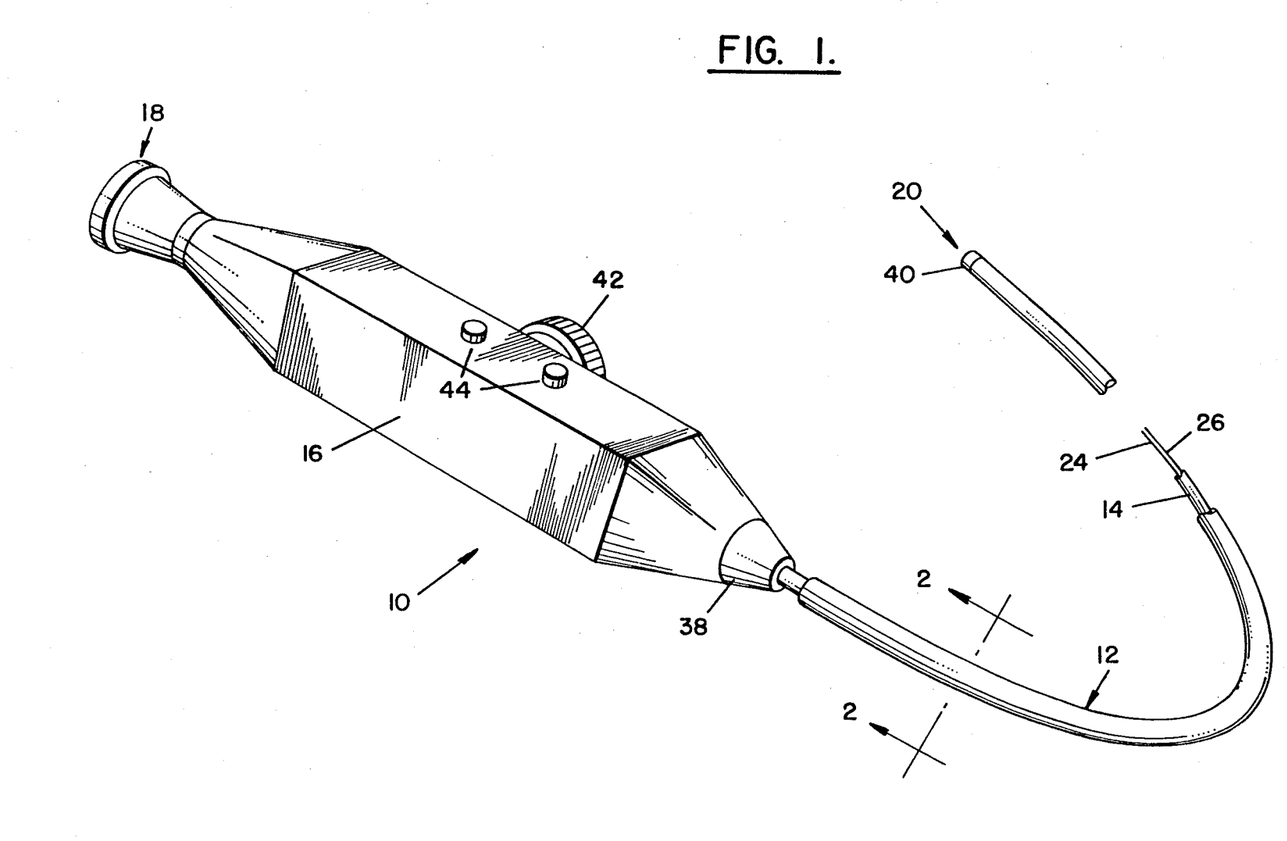
FIG. 1 is a perspective illustration of the preferred embodiment of the present invention illustrating the combination of an endoscope and disposable, sanitary sheath positioned upon the endoscope.
Figure 3:
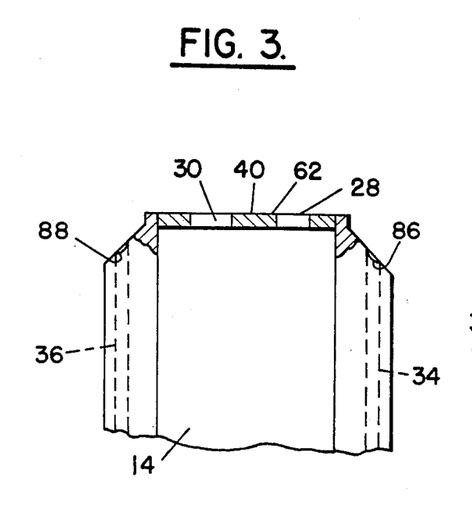
FIG. 3 is an enlarged perspective illustration of the front or distal end of the apparatus shown in FIG. 1.

FIG. 1 shows an endoscope 10 in combination with a disposable, sanitary sheath 12. The endoscope includes a flexible core 14 extending from a headpiece 16 at the back or proximal end 18 of the endoscope. The core terminates at a front or distal end 20. The core is thus located between the distal end 20 and the headpiece 16. The core includes optical means 24 and 26. Optical means 24 is for illuminating the image. Optical means 26 is for conveying the image from the distal end of the core to adjacent the headpiece for diagnostic purposes. As is known in the art of endoscopy, any number of optical devices for illumination and viewing purposes may be incorporated into endoscopic instruments for performing the intended functions. For example, the distal end of the core may contain a lens which may be optically coupled to the headpiece as through a fiber optic bundle. In addition, or in the alternative, other optical structures or devices may be incorporated into the core and utilized. Regardless of the structures used, the core will preferably have, optically transparent windows 28 and 30 as shown in FIG. 3, or in the alternative, one such window, at or near its distal end for illuminating and viewing a remote organ or other part of a patient to be examined and some apparatus for optically or electrically coupling this image to the headpiece for observing the remote part of the patient being examined or treated.

The illuminating structure 24 may take the form of a fiber optic bundle extending from the headpiece to adjacent the window at the distal end of the core. The bundle may be coupled to a light source (not shown). As an alternative, the light may be located directly at the distal end of the core, with the light being powered through wires extending from the headpiece through the core. In either case, light must be directed from the distal end of the core to the part of the patient that is to be viewed.

Figure 2:
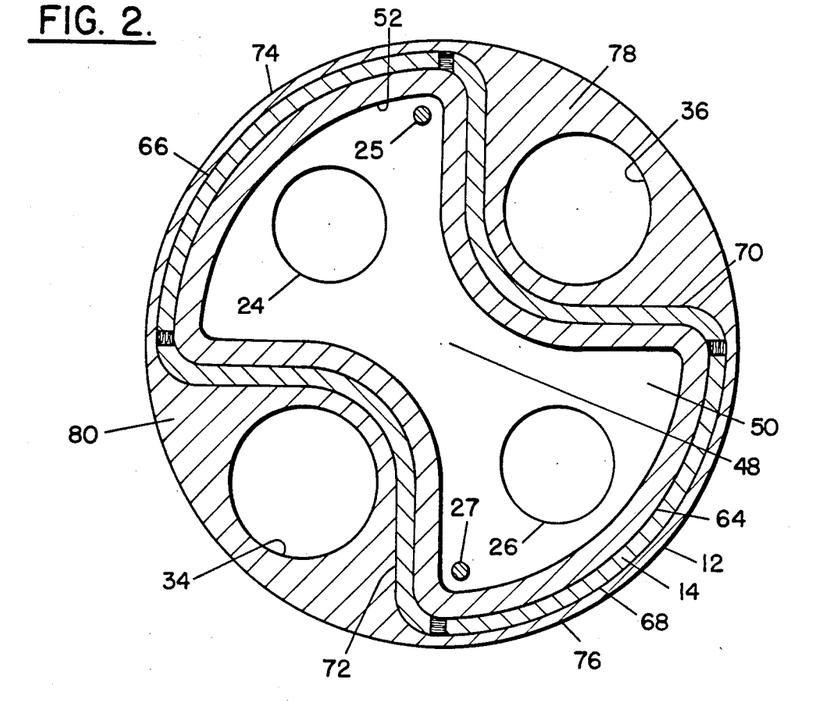
FIG. 2 is an enlarged sectional view of the apparatus illustrated in FIG. 1 taken along line 2—2 of FIG. 1.

Referring now also to FIG. 2, the above-described structures are for observation and diagnostic purposes. Endoscopes also may serve therapeutic purposes. This is possible by virtue of auxiliary functioning tubes or channels 34 and 36 extending from the headpiece 16 at the proximal end 38 of the core 14 to the distal end 40 of the core for performing a wide variety of functions. One of these tubes may be used to inject air, carbon dioxide, or other gas to distend the observed organ of a patient and permit more thorough visual inspection and treatment. A tube extending the length of the endoscope core may also be used with mechanisms to extract or to inject fluids into the body of the patient. Finally, various other devices or mechanisms, both diagnostic and therapeutic, may be inserted through the endoscopic channels 34 and 36 perform one or more of a wide variety of specific functions such as biopsy removal, stone disengagement, or the like, from the distal end of the endoscope in manners well known in the art. If the endoscope is merely for diagnostic purposes, and not therapeutic purposes, the endoscope can have optical means 24 and 26 without any channels. The front or distal end 40 of the core 14 is thus closed in that no open channel terminates thereat for the flow of fluids or placement of mechanisms or the like through the core. This allows the distal end of the core to be covered by a sheath. Functioning channels 34 and 36 extending to and through the distal ends of cores are common in most presently commercial endoscopes.

To a large extent, the usefulness of commercially available endoscopes may depend upon the ability of the physician to manipulate the position of the distal end of the core while it is located within the body of a patient. Such manipulation may normally be accomplished by retracting control cables 25 and 27 located within the core. Such control cables may be anchored near the distal end of the core. They may extend along the length of the core to knobs 42 on the headpiece under the control of the physician. The knobs may be rotated to move the distal end of the core in directions of the one or two major orthogonal axes or meridians. The core must also be movable or flexible to conform with the orifice being examined. Additional valves, actuated by additional control knobs 44, regulate the flow of fluid through the various functioning channels 34 and 36.

The preferred or primary embodiment of the inventive endoscope-sheath combination is illustrated in FIGS. 1 through 5. FIG. 2 is a cross-sectional view of the endoscope 10 and core 14 taken along lines 2—2 of FIG. 1. As can be seen in FIG. 2, the core is generally symmetric about a central axis 48. The central portion 50 of the core is hollow except for the optical members 24 and 26 and two control cables 25 and 27. The optical members 24 and 26 may preferably include a fiber-optic bundle or the like for illumination and an additional fiber-optic bundle for remote viewing of the illuminated area of the patient being examined. The bundles extend from the front or distal end 40 of the core to the back or proximal end 38 of the core and also extend into the headpiece 16 for operator control and convenience. The ends of the optical members 28 and 30 extend to apertures or windows 28 and 30 in the distal end of the core. The core 14 at the distal end 40 is closed to prevent any foreign material from contaminating the core.

Figure 5:
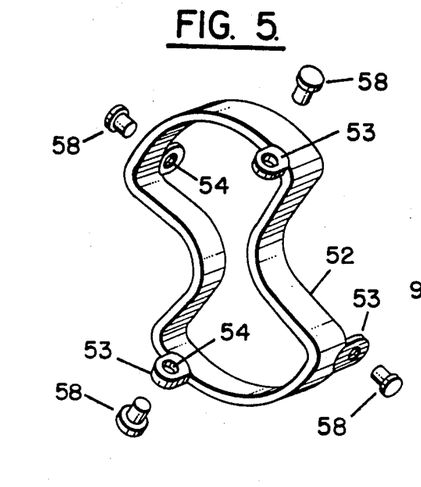
FIG. 5 is an enlarged perspective illustration of one of the internal segments used to constitute the internal portion of core of the endoscope.

The interior-most portion of the core structure is made up of a plurality of discrete segments 52. FIG. 5 shows an enlarged view of a segment 52. Each segment 52 has apertured projections 53 with attachment apertures 54 in pairs facing oppositely in axial directions. In this embodiment, the aperture projections 53 are 90 degrees from each next adjacent projection. Pins 58 are provided for coupling the segments 52, one to another, for limited pivoting of the cores segments in one or two orthogonal directions or meridians. This provides universal movement and flexibility to the core. The distal end of the core as shown in FIG. 3, is formed as a planar right circular cylinder member which forms an end cap 62 similarly pinned to the distal-most segment of the core. The segments 52 and end cap 62 are preferably formed of a metal such as stainless steel, but could be made of any suitable material.

Figure 8:
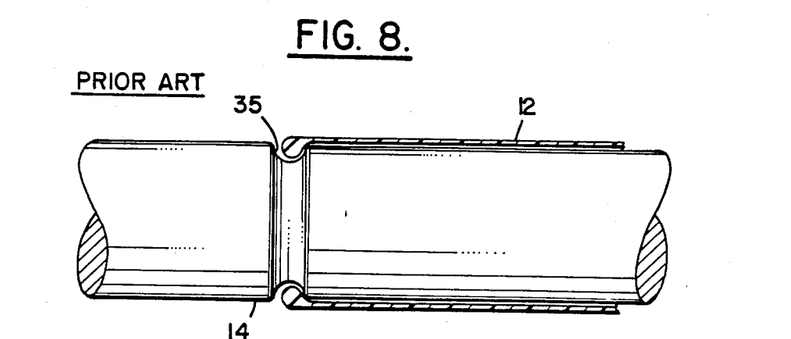
FIG. 8 is a perspective illustration of a prior art end coupling between a flexible core and sheath.

FIG. 8 shows a portion of a typical rolled on shield. The shield 12 would be rolled onto the core 14 and retained in the depression 35. However, even with this type of a shield bodily fluid and tissue might still contact non-disposable portions of the endoscope.

Referring back to FIG. 2, exterior to the segments 52 in the construction of the core is an essentially tubular spiral covering 64. The spiral covering 64 is generally made of a material such as stainless steel, but may be made of any other suitable material. The tubular spiral covering 64 has two layers coiled in a spiral fashion to form a flexible, yet torque stable support of the instrument shaft. The two layers of the spirals in the covering 64 are each wound in opposite directions from one another thus providing the torque stabilizing feature of the shaft.

In the embodiment shown in FIG. 2, the core has a cross-sectional configuration with essentially circular outer-most surfaces or extended segments 66 and 68 extending over two 90 degree regions diametrically opposed to each other. Circimferentially between these extended segments are two diametrically opposed indented or recessed segments 70 and 72. The cross-section of the core thus constitutes a peanut-shaped configuration. It is within these indented segments that the functioning channels 34 and 36 of the sheath are located. The exterior surface profile of the core, with both extended segments and indented segments, as shown in FIG. 2, extends the entire length of the core from the first or distal end of the core to the second or proximal end of the core.

Figure 4:
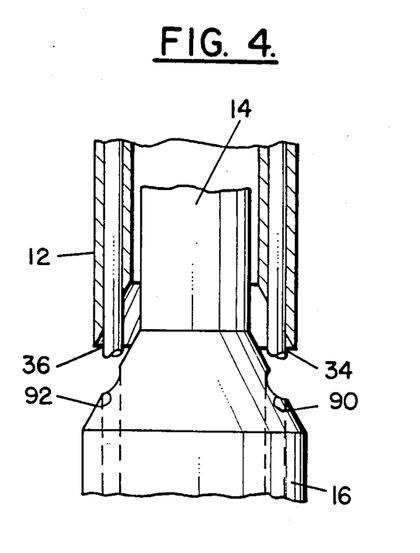
FIG. 4 is an enlarged perspective illustration of the apparatus illustrated in FIG. 1 showing the back or proximal end of the sheath.

Formed independently of the core is the sheath 12. The sheath is fabricated of a flexible, resilient, elastomeric material capable of being extruded or molded very thin. The material is fluid impervious so that when placed upon the core it will preclude fluids from penetrating the exterior surface of the sheath internally to the exterior surface of the core. The sheath is provided with two relatively thin wall sections 74 and 76 which overlie those extended segments 66 and 68 of the core between the indented segments or portions. Circumferentially between the thinner sections of the sheath are longitudinally enlarged or thicker segments or portions 78 and 80 adapted to be received within the indented segments 70 and 72 of the core. Each of the thicker portions 78 and 80 can have a functioning channel 34 and 36 as shown in the embodiment in FIG. 2. The channels or tubes 34 and 36 travel from the distal end 40 of the sheath through the sheath, longitudinally, and exit the sheath 12 to travel to an instrument entry port in the headpiece or to an external air or water pump (not shown). The channels or tubes 34 and 36 exit the distal end 40 of the sheath at apertures 88 and 86 and thus provide a continuous tubing from the distal end 40 to the instrument entry port in the headpiece or air or water pump (not shown). The tubes 34 and 36 may exit the sheath 12 near the headpiece 16 and be attached to the exterior of the headpiece 16. In addition, or in the alternative, the tubes 34 and 36 may exit the sheath 12 near the headpiece 16 and travel through at least a portion of the interior of the headpiece 16. In such an embodiment, as shown in FIG. 4, the channels 36 and 34 would become tubes 36 and 34 which could travel into the headpiece 16 through openings 90 and 92. The distal end 40 of the sheath is transparent to allow the proper functioning of the optical structures in a manner similar to the transparent covering and may have a clear plastic cap. In the alternative, the entire sheath may be transparent.

Figure 6:
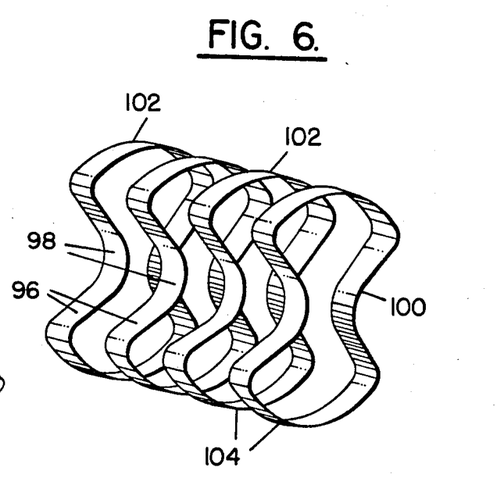
FIGS. 6, and 7 are perspective illustrations of alternate embodiments of structures functioning similarly to that as shown in FIG. 5.
Figure 7:
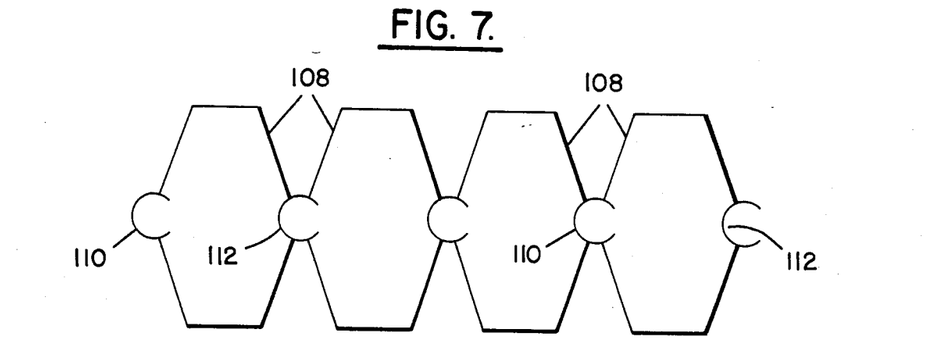

Alternate or secondary forms of construction for the interior of the core beneath the cover are shown in FIGS. 6 and 7. In the FIG. 6 embodiment, the segments 96 are formed as permanently coupled segments of material such as stainless steel or any other suitable material. The segments are formed as a continuous coil so that universal flexibility is provided to the core in a manner similar to the segments of the primary embodiment. The coil is formed with recessed or indented portions 98 and 100 and extended portions 102 and 104 in its cross-sectional configuration so that when provided with a covering, the core will appear to be identical with the core of the primary embodiment.

A yet further embodiment of the segments is shown in FIG. 7. In the FIG. 7 embodiment, each segment 108 is provided with indented and extended portions similar to those described with respect to FIG. 5. Each segment is also provided with couplable pairs of projections 110 and recesses 112 aligned in the direction of the axis of the core. When snapped together, the segments 108 form the interior structure of the core. No pins are required to effect the coupling of the segments. Unlike the FIGS. 5 and 6 embodiments, the FIG. 7 embodiment is flexible only in one orthogonal direction or meridian.

Figure 9:
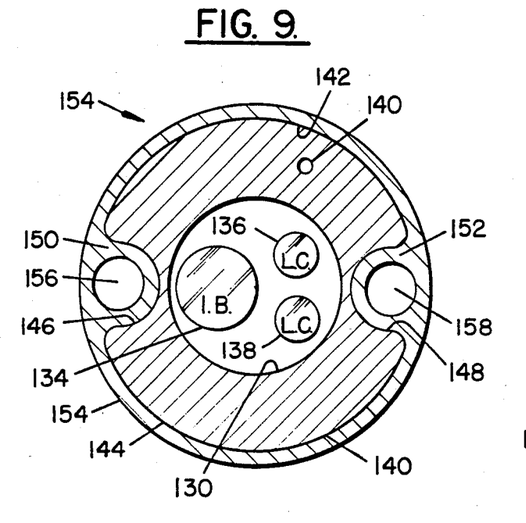
FIGS. 9 and 10 are sectional views of alternate embodiments of endoscope cores wherein the shields may be utilized with existing endoscopes having circular cross-sectional configurations.
Figure 10:
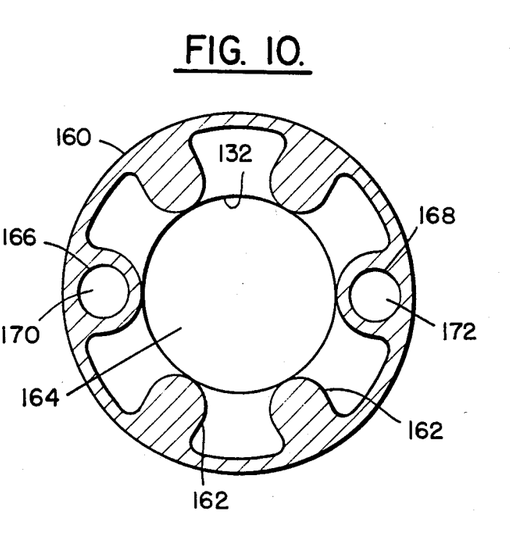

Additional alternate or secondary embodiments of the invention are shown in FIGS. 9 and 10. These embodiments are similar to the prior embodiments in that they may utilize a core with a closed end in combination with a channeled sheath. These embodiments, however, differ from those described above since the core 130 and 132 is of a circular crosssectional configuration. These configurations represent typical endoscopes in use today which can be modified to have a disposible sheath. As shown in FIG. 9, the circular core 130 is provided with optical members 134, 136 and 138 terminating at the distal end of the core and having no functioning channel openings. Supported on the circular exterior surface of the core is a sleeve 140 formed of a material such as an extruded elastomeric polyurethane foam of sufficient rigidity as not to radially deform during operation and use. The exterior or extended segments 142 and 144 of the surface of the sleeve is essentially circular over the majority of its extent except for two diametrically opposed indented or recessed portions 146 and 148 which extend along the entire length of the sleeve. This length is generally longer than the entire length of the core. The length of the sleeve is generally equal to the entire length of the core, however, the portions of the sleeve can extend past the core. The portions of the sleeve that extend past the core are thickened portions 150 and 152 that contain the channels or tubes 156 and 158. The tubes thus extend past the core to terminate at devices such as an instrument entry port in the headpiece or air/water generator (not shown). As in the prior embodiments, the indented portions of the sleeve are adapted to receive the thickened portions 150 and 152 of the sheath 154 containing the functioning channels 156 and 158.

The use of a sleeve in association with a circular core 132 is obviated by the sheath design of FIG. 10. In accordance with the FIG. 10 embodiment, the sheath 160 is formed with a circular exterior cross-sectional configuration, hollow in the middle, but with internally extending ribs or projections 162 radially directed toward the axis 164 of the core. The projections extend inwardly periodically to contact the external surface of the core. They extend longitudinally from the distal to the proximal ends of the core. Two of the radially inward directing projections 166 and 168 are circumferentially enlarged and are formed with the functional channels 170 and 172 of the sheath.

Figure 11:
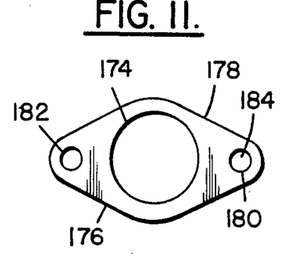
FIGS. 11, 12 and 13 are sectional views of yet further alternate embodiments of endoscope cores wherein the shields may be utilized with existing endoscopes having circular cross-sectional configurations.
Figure 12:
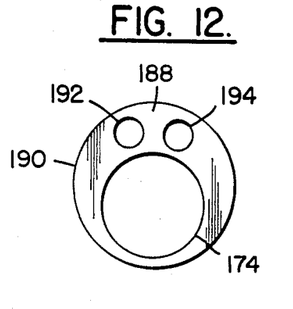
Figure 13:
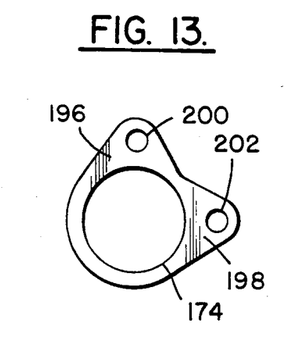

The last embodiments of the core-sheath combination are shown in FIGS. 11, 12 and 13. These embodiments are adapted for use on a core 174 with a circular cross-sectional configuration similar to the embodiments of FIGS. 9 and 10. The external surface of these cores support the internal surface of the variously designed sheaths. The sheath 176 is provided with two thickened sections 178 and 180 in the FIG. 11 embodiment with each thickened section supporting a functioning channel 182 and 184. The two thickened sections are located 180 degrees apart. A single enlarged section 188 is provided on the sheath 190 of the FIG. 12 embodiment. The enlarged thickened portion allows two closely spaced functioning channels 192 and 194 to be provided in the sheath. The last embodiment, that of FIG. 13, has two thickened portions 196 and 198, each with a functioning channel 200 and 202. The channels are spaced 90 degrees from each other rather than more closely spaced as in the FIG. 12 embodiment and rather than more distantly spaced as in the FIG. 11 embodiment. These embodiments, like the embodiments of FIGS. 9 and 10, are more susceptible for use with presently commercially available endoscopes with their circular cross-sections. The last three embodiments, however, create a combination of endoscope and sheath with a non-circular cross-sectional configuration which may cause some additional discomfort to a patient during an examination although they represent the most efficient utilization of the least amount of volume.

The embodiments of FIGS. 9 through 13 require a smaller diameter core than the embodiments of FIGS. 1 through 8 since the axes of the functioning channels are entirely exterior of the external surfaces of the cores. In contrast to this, the cores of the embodiments disclosed in the first eight Figures have the axes of their functioning channels radially interior of the exterior-most surface or extended segments of the core, being within the indented or recessed portions. The embodiments of FIGS. 1 through 8 thus require specially designed cores.

Figure 14:
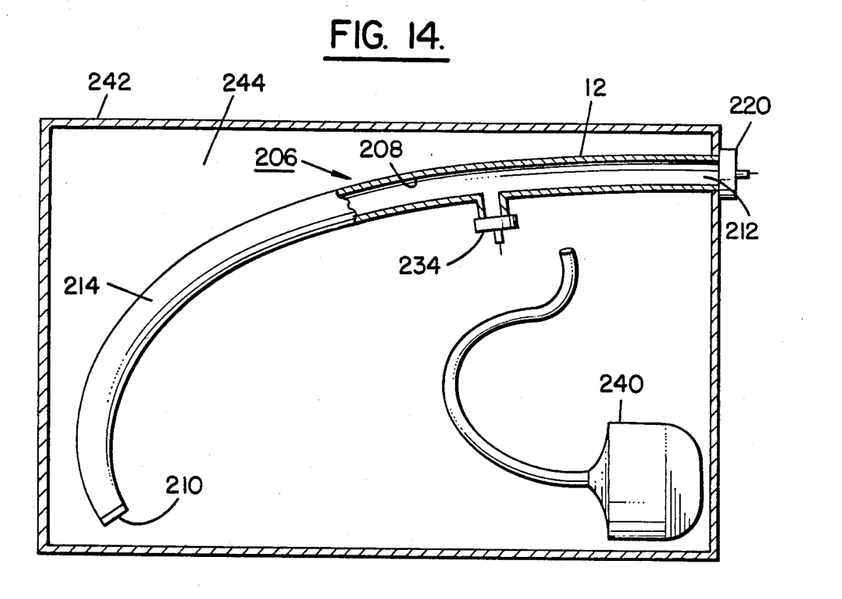
FIG. 14 is a perspective illustration of the combination of a tube and suction device for the installation of a sheath upon the endoscope and for the removal therefrom.
Figure 15:
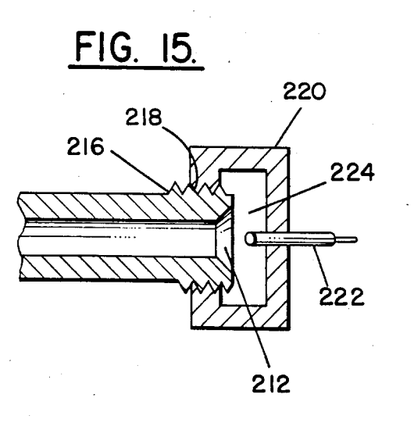
FIG. 15 is an enlarged sectional view of the proximal end of the tube shown in FIG. 14.
Figure 16:
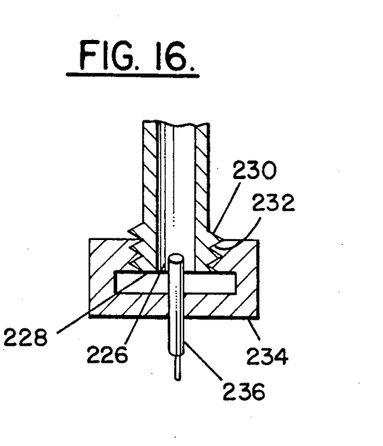
FIG. 16 is an enlarged sectional view of the tube illustrated in FIG. 14 showing the intermiate portion and second opening and cap.

The present invention is for an apparatus and method for placement of a sheath upon the core of an endoscope and also for its removal from the endoscope. The sheath may be any of the many standard sheaths presently commercially available or the peanut-shaped device as described above. The apparatus is adapted for the removal of such sheaths from such an endoscope and also for the eventual disposal of the entire insertion/removal apparatus with the used sheath. The apparatus for such installation and removal of sheaths is shown in FIGS. 14, 15 and 16. The key element is a tubular member or tube 206 of a relatively rigid air-impervious material such as a highly vulcanized rubber, natural or synthetic, or blends thereof. The tube 206, tapered or non-tapered, is shaped to have an interior surface 208 similar in shape to that of the core upon which the sheath is to be placed. The length of the tube is the same as the core. For the sake of descriptive purposes, the tube will be described for use in association with the sheath and core of the primary or preferred embodiment as illustrated in the FIGS. 1 through 5.

As shown in FIG. 14, although configured with its interior surface shaped similarly to the exterior surface of the core, the tube 206 is of a slightly larger cross-sectional configuration and is also tapered being largest at the opening and narrower at its distal end. Its first or distal end 210 is made of a resilient rubber-like material or any other suitable material for sealing the front face against the instrument sheath. The first end 210 is closed while its second or proximal end has an opening 212 for the receipt of an endoscope core, both for installation or removal of its associated sheath. The axis 214 of the tube is co-extensive with the axis 48 of the inserted endoscope core. As can be more clearly seen in FIG. 15 the proximal end of the tube is provided with external threads 216 which detachably couple with internal threads 218 on an axial or first cap 220 to retain the interior of the tube pressurized prior to use. A one-way valve 222 is provided in the cap for the addition of pressurized air to interior of the tube. The proximal end of the tube is also provided with a circular conformable shoulder or seat 224 for purposes to be later described.

An intermediate portion of the tube is formed with a radial or second opening 226 surrounded by a radially extending cylindrical extension with lip 228 and external threads 230 for detachably coupling with internal threads 232 of a second cap 234. The second cap, like the first cap, is provided with a valve 236. The valve of the second cap, however, is a one-way valve through which a vacuum may be drawn within the tube. A hand-held suction creating device in the form of a bellows 240 is preferably provided with each tube or tubular member for convenience to the operator. The tube with caps 220 and 234 in place, in combination with the bellows 240, are preferably supported as on a member 242 made of rigid plastic or any other suitable material, encased in a clear heat-shrunk plastic 244, for distribution and sale as a blister-pack, a preferable arrangement for handling purposes and operator convenience.

A sheath 12 is provided within each tube 206 with its functioning channels 34 and 36 and thickner portions 78 and 80 in a predetermined orientation, preferably marked with indicia on the exterior surface of the tube 206 as an aid in aligning the indented portions 70 and 72 of the core 14 with the thicker portions 78 and 80 of the sheath 12. Upon an operator receiving the tube 206, the sheath 12 will have been previously placed within the tube in proper orientation with high pressure vacuum distending the sheath against the interior surface 208 of the tube and with air pressure created through the valve 220 assisting in holding the sheath against this desired orientation.

The present invention yet further contemplates the method of utilizing the above-described apparatus to install or place a sheath 12 in proper orientation upon a core 14 of an endoscope 10 as well as for its removal therefrom after the combination core-sheath has been used for examining a patient. To place a sheath on a core of an endoscope, the operator first removes the first cap 220 from the tube 206 whereby the open end 212 of the tube may readily receive the core of the endoscope. The endoscope core is then inserted entirely within the tube. The core and tube are formed of equal lengths. The distal end of the core will contact and bottom on the interior distal end of the tube while the junction between core and headpiece will form a temporary seal with the cylindrical conformable seat 224 at the proximal end of the tube. The operator then removes the second cap 234 which thereby relieves the vacuum between tube 206 and sheath 12. It was this vacuum which had been holding the sheath against the tube and away from the core. The sheath 12 thus releases itself from the tube 206 and snaps into position onto the external surface of the core 14 by virtue of the equalization of pressures on both sides of the sheath and also by virtue of the resiliency of the sheath.

In order to remove a sheath 12 from an endoscope core 14 after usage on a patient, the operator inserts the endoscope-sheath combination back into the tube 206 with the first cap 220 and the second cap 234 removed. The distal end of the sheath and core will contact and bottom on the interior distal end 210 of the tube. The interface between core and headpiece will form a temporary seal on the conformable seat 224 at the proximal end of the tube. The distal end of the instrument/sheath is placed firmly against the stop 210. The open distal end is then sealed against the linkage of removal vacuum. The second cap 234 is then coupled onto the lip to effectively close the second opening 226 and thereby make an airtight seal within the tube. The valve 236 is then utilized with the bellows 240 or other source of negative pressure to draw a vacuum in the tube between the tube and sheath. In the alternative, the tube of the bellows 240 could be placed directly over the valve 236. The action of the negative pressure in combination with the resilience of the sheath 12 will draw the sheath away from the core 14. Thereafter the core may be withdrawn from the tube ready for receiving a new sterilized sheath 12 from a new tube 206 in the manner as described above. The previously used sheath 12, tube 206, caps 220 and 234 and bellows 240 may then be discarded.

While the present invention has been described with respect to a preferred embodiment and alternate or secondary embodiments, the invention is not intended to be so limited but it is intended to be protected broadly within the spirit and scope of the appended claims.

What is claimed is:

1. Apparatus to facilitate the placement of a sheath upon the core of an endoscope and to facilitate its removal therefrom, the apparatus comprising a tube of relatively rigid, air-impervious material having an internal configuration similar to that of the core upon which the sheath is to be placed but of a slightly larger cross-sectional configuration, the tube having a closed distal end and an open proximal end for receiving the endoscope, the proximal end being provided with a removable first cap axially located with respect to the tube, the tube being provided with a second removable cap at an intermediate portion of the tube and radially located with respect to the tube whereby a sheath may be inserted into the tube with the first cap removed and the second cap unremoved to maintain the air pressure within the tube greater interior of the sheath than exterior of the sheath for holding the sheath in position against the interior surface of the tube for thereby allowing the positioning of the endoscope within the sheath and tube, the radial cap being removable for the relief of the lower pressure exterior of the sheath for the release of the sheath from the tube and onto the core, a coupling lip on the tube for supporting the radial cap and for coupling with a source of negative pressure whereby when a core with a sheath thereon is positioned within the tube, a vacuum may be drawn through the lip in the tube external of the sheath to pneumatically separate and remove the sheath from the endoscope.

2. An apparatus as in claim 1 wherein said tube of relatively rigid, air-impervious material is tapered.

3. An apparatus as in claim 1 wherein said tube has at least two coupling lips.

4. Apparatus to facilitate the placement of a sheath upon the core of an endoscope, the apparatus comprising a tube of relatively rigid, air-impervious material having an internal configuration similar to that of the core upon which the sheath is to be placed but of a slightly larger cross-sectional configuration, the tube having a closed distal end and an open proximal end for receiving the endoscope, the proximal end being provided with a removable first cap axially located with respect to the tube, the tube being provided with a second removable cap at an intermediate portion of the tube and radially located with respect to the tube whereby a sheath may be inserted into the tube with the first cap removed and the second cap unremoved to maintain the air pressure within the tube greater interior of the sheath than exterior of the sheath for holding the sheath in position against the interior surface of the tube for thereby allowing the positioning of the core within the sheath and tube, the radial cap being removable for the relief of the lower pressure exterior of the sheath for the release of the sheath from the tube and onto the core.

5. An apparatus as in claim 4 wherein said tube is tapered.

6. An apparatus as in claim 4 wherein said tube has at least two removable caps.

7. Apparatus to facilitate the removal of a sheath from the core of an endoscope, the apparatus comprising a tube of relatively rigid, air-impervious material having an internal configuration similar to that of the core with the sheath thereon but of a slightly larger cross-sectional configuration, the tube having a closed distal end and an open proximal end for receiving the core with the sheath thereon, the proximal end being provided with a removable first cap axially located with respect to the tube, the tube being provided with a second removable cap at an intermediate portion of the tube and radially located with respect to the tube whereby an endoscope with a sheath thereon may be inserted into the tube with the first and second caps removed, a coupling lip on the tube for supporting the second or radial cap and, in the absence of the radial cap, for coupling with a source of negative pressure whereby when a core with a sheath thereon is positioned within the tube, a vacuum may be drawn through the lip in the tube external of the sheath to pneumatically separate and remove the sheath from the endoscope.

8. An apparatus as in claim 7 wherein said tube is tapered.

9. An apparatus as in claim 7 wherein said tube has at least two removable caps at intermediate portions of the tube.

10. The apparatus as set forth in claim 7 and further including suction means to create the vacuum for removing the sheath from the endoscope.

11. A method to place a sheath upon the core of an endoscope and to remove it therefrom, the method including the steps of:
providing a tube of relatively rigid, air-impervious material having an internal configuration similar to that of the core to be provided with the sheath but with a cross-sectional configuration slightly larger than that of the core, the tube having a distal end which is closed and a proximal end which is open for the receipt of the core;
positioning a sheath within the tube;

supporting the sheath against the interior surface of the tube by a pressure differential between the interior and exterior of the sheath;

inserting a core into the tube;

equalizing the pressure differential between the interior and exterior surfaces of the sheath for the release of the sheath from the tube and its placement onto the core;

removing the core with the sheath from the tube;

inserting a core with a sheath into the tube; and drawing a vacuum in the tube between the tube and the sheath to pneumatically remove the sheath from the core.

12. A method as in claim 11 wherein said tube is tapered.

13. A method to facilitate the placement of a sheath upon the core of an endoscope and its removal therefrom, the method including the steps of:

providing a tubular member of relatively rigid, air-impervious material having an internal configuration similar to that of the core to be provided with the sheath but with a cross-sectional configuration slightly larger than that of the core, the tubular member having a distal end which is closed and a proximal end which is open for the receipt of the core and a second opening intermediate the ends;

positioning a sheath within the tubular member;

supporting the sheath against the interior surface of the tubular member by a pressure differential between the interior and exterior of the sheath;

removing a cap from the open end of the tubular member;

inserting a core into the tubular member;

removing a cap from the second opening to equalize the pressure differential between the interior and exterior surfaces of the sheath for the release of the sheath from the tubular member and its placement onto the core;

removing the core with the sheath from the tubular member;

inserting a core with a sheath into the tubular member; and drawing a vacuum in the tube between the tube and the sheath through the second opening to pneumatically remove the sheath from the core.

14. A method as in claim 13 wherein said tubular member is tapered.

15. A method of placing a sheath upon the core of an endoscope, the method including the steps of providing a tube of relatively rigid, air-impervious material having an internal configuration similar to that of the core to be provided with the sheath but with a cross-sectional configuration slightly larger than that of the core, the tube having a distal end which is closed and a proximal end which is open for the receipt of the core; positioning a sheath within the tube; supporting the sheath against the interior surface of the tube by a pressure differential between the interior and exterior of the sheath; inserting an endoscope into the tube; equalizing the pressure differential between the interior and exterior surfaces of the sheath for the release of the sheath from the tube and its deposition onto the endoscope.

16. A method as in claim 15 wherein said tube is tapered.

17. A method of removing a sheath from an endoscope, the method including the steps of providing a tube of relatively rigid, air-impervious material having an internal configuration similar to that of the core to be provided with the sheath but with a cross-sectional configuration slightly larger than that of the endoscope with the sheath, the tube having a distal end which is closed and a proximal end which is open for the receipt of the endoscope; inserting an endoscope shielded by a sheath into the tube; and drawing a vacuum in the tube between the tube and the sheath to pneumatically remove the sheath from the endoscope.

* * * * *